(12) United States Patent
Jin et al.

(10) Patent No.: US 9,924,868 B2
(45) Date of Patent: Mar. 27, 2018

(54) METHOD, APPARATUS, SYSTEM, AND COMPUTER READABLE MEDIUM FOR DETERMINING PREFERABLE CONDITIONS FOR MAC COMMUNICATION WITHIN A WBAN

(71) Applicant: KABUSHIKI KAISHA TOSHIBA, Tokyo (JP)

(72) Inventors: Yichao Jin, Bristol (GB); Stephen Wang, Bristol (GB)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 15/510,144

(22) PCT Filed: Dec. 9, 2014

(86) PCT No.: PCT/GB2014/053640
§ 371 (c)(1),
(2) Date: Mar. 9, 2017

(87) PCT Pub. No.: WO2016/092241
PCT Pub. Date: Jun. 16, 2016

(65) Prior Publication Data
US 2017/0347887 A1    Dec. 7, 2017

(51) Int. Cl.
*H04B 7/00* (2006.01)
*A61B 5/00* (2006.01)
*H04B 13/00* (2006.01)
*H04W 4/00* (2018.01)
*A61B 5/11* (2006.01)
*H04L 29/08* (2006.01)
*H04W 88/08* (2009.01)

(52) U.S. Cl.
CPC .......... *A61B 5/0024* (2013.01); *A61B 5/1123* (2013.01); *H04B 13/005* (2013.01); *H04L 67/306* (2013.01); *H04W 4/005* (2013.01); *A61B 2560/0209* (2013.01); *H04W 88/08* (2013.01)

(58) Field of Classification Search
None
See application file for complete search history.

(56) References Cited

U.S. PATENT DOCUMENTS

| 8,989,053 B1* | 3/2015 | Skaaksrud ............ H04W 12/06 370/255 |
| 2014/0274044 A1* | 9/2014 | Lee ........................ H04W 48/16 455/434 |
| 2015/0382086 A1* | 12/2015 | Kim ...................... A61B 5/1116 340/870.07 |

OTHER PUBLICATIONS

IEEE Standards Association, "IEEE Standard for Low-Rate Wireless Networks", IEEE Computer Society, sponsored by the LAN/MAN Standards Committee, IEEE Std 802.15.4™-2015, Revision of IEEE Std 802.15.4-2001 pp. 1-707, (2015).

* cited by examiner

*Primary Examiner* — Mohammed Rachedine
(74) *Attorney, Agent, or Firm* — Finnegan, Henderson, Farabow, Garrett & Dunner, L.L.P.

(57) ABSTRACT

A method for use within a WBAN, the method comprising creating a motion profile and a corresponding channel quality profile and using the motion profile to determining preferable conditions for MAC communication within the WBAN.

14 Claims, 10 Drawing Sheets

METHOD, APPARATUS, SYSTEM, AND COMPUTER READABLE MEDIUM FOR DETERMINING PREFERABLE CONDITIONS FOR MAC COMMUNICATION WITHIN A WBAN

FIELD

This disclosure relates to Wireless Body Area Networks (WBANs). In particular, but without limitation, this disclosure relates to the determination of preferable conditions for MAC communication within a WBAN.

BACKGROUND

As a result of aging populations and rising costs of medical treatments and investigations, e-healthcare has become increasingly important. In e-healthcare systems, wearable or implantable sensors are used to monitor vital healthcare signs and report data to a relatively powerful device called a hub or coordinator device—which may, for example, take the form of a PDA (Portable Data Assistant), cell phone, or bedside monitoring point. Instead of traditional wired connection, a WBAN is built to wirelessly connect bodily sensors which can enable functionality such as 24/7 real-time monitoring services for elderly and other patients in need.

SUMMARY

Aspects and features of the invention are set out in the claims.

BRIEF DESCRIPTION OF THE DRAWINGS

Examples of the present disclosure will now be described with reference to the accompanying drawings in which.

DETAILED DESCRIPTION

Figure 1:
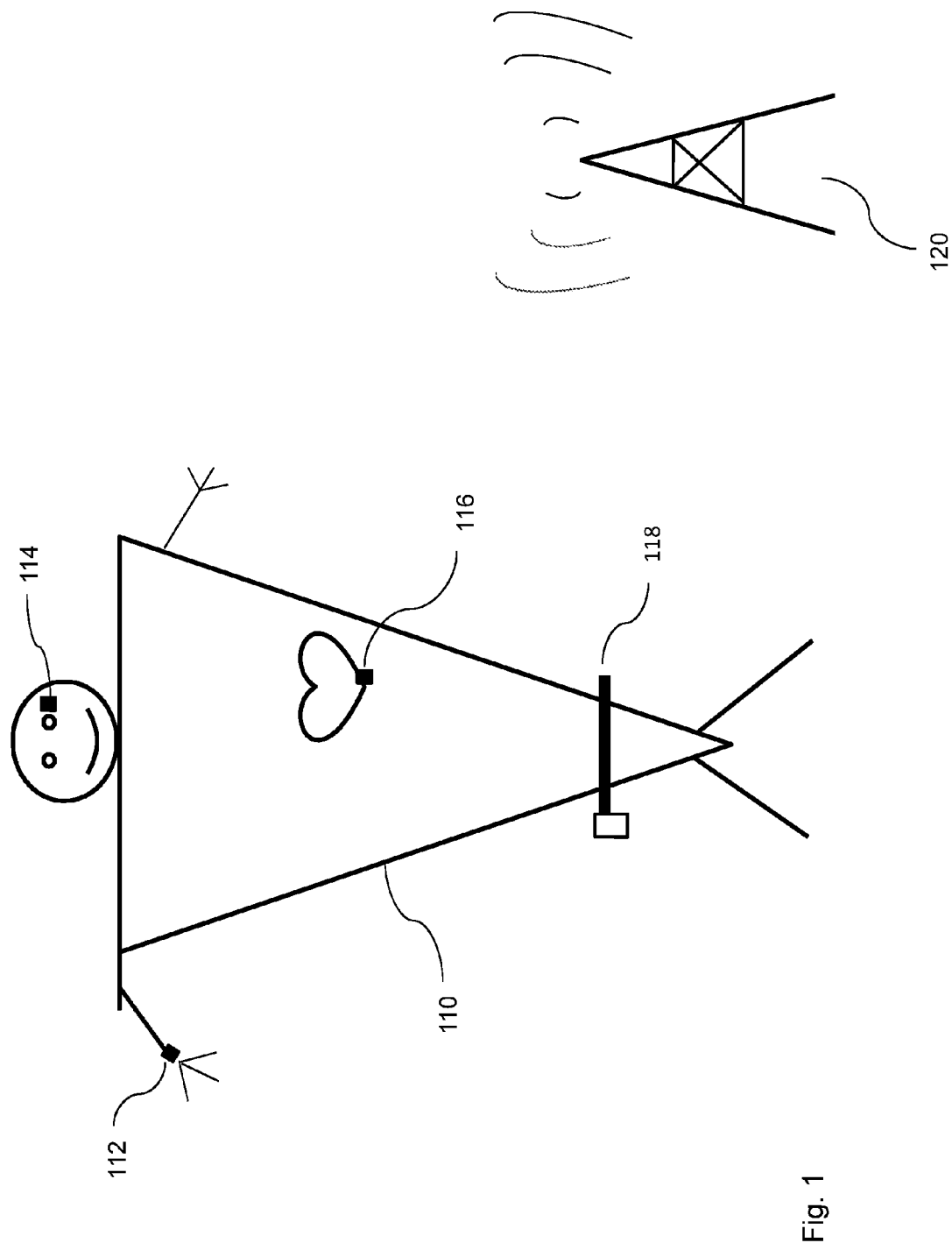
FIG. 1 shows a cartoon of a person that is wearing a plurality of wireless devices.

FIG. 1 shows a cartoon of a person 110 that is wearing a plurality of wireless devices that are arranged to communicate wirelessly with one another so as to form a wireless body area network having a star-shaped topology. In this example, a hub node 112 is worn by the person 110 on their wrist and is arranged to communicate with peripheral nodes 114, 116, and 118. A person skilled in the art will understand that the hub node need not be located on the person's wrist and could be located elsewhere—for example on the person's chest or waist. The hub node 112 and/or the peripheral nodes 114, 116, and 118 may have sensors configured to sense one or more aspects of the person's physiology. For example, the hub node 112 may be arranged to monitor blood oxygen levels and/or pulse rates, peripheral node 114 may be arranged to monitor intra-ocular pressure, peripheral node 116 may be coupled to a pacemaker and arranged to monitor and/or control cardiac pacing, and peripheral node 118 may be a mobile device such as a mobile telephone that is being carried on the users waist. One or more of the nodes may be arranged to further communicate with distance wireless network with a base station 120. In this example, peripheral node is a mobile device 118 is arranged to communicate with the base station 120.

Figure 2:
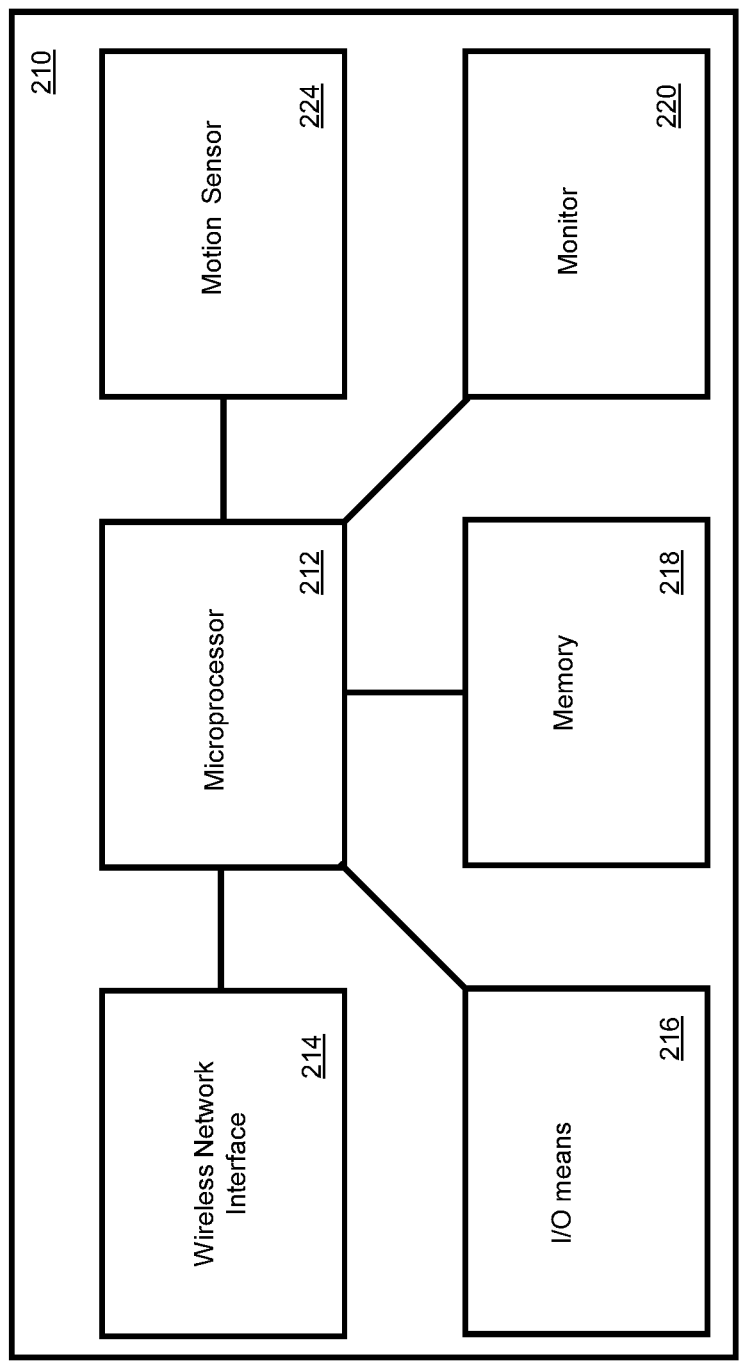
FIG. 2 shows an exemplary block diagram of the macro components of a wireless node.

FIG. 2 shows an exemplary block diagram of the macro components of a wireless node 210 for example a hub or peripheral node. The wireless node 210 comprises a microprocessor 212 arranged to execute computer readable instructions as may be provided to the wireless node 210 via one or more of a wireless network interface 214 having an antenna (not shown) and being arranged to enable the microprocessor 212 to communicate with a network—for example a WBAN and optionally another network such as the internet; a plurality of input/output interfaces 216 which may include one or more buttons, touch screen, a keyboard and a board connection (for example a USB connection), and interfaces for one or more physiology sensors such as blood oxygenation sensors, pulse rate sensors, intra-ocular pressure sensors, cardiac pacing sensors, cardiac stimulation interfaces, etc.; and a memory 218 that is arranged to be able to retrieve and provide to the microprocessor 212 instructions and data that has been stored in the memory 218. The microprocessor 212 may further be coupled to a monitor (for example a screen on a smart watch) upon which a user interface may be displayed and further upon which the results of processing/or sensing operations may be presented. The wireless node 210 further comprises a motion sensor 224 (for example an accelerometer) arranged to provide a motion signal to the microprocessor 212 when the wireless node 210 is moving.

When a person is moving—for example walking, rowing, running on a treadmill, or performing other repetitive and thus periodic activities, the spatial relationships between nodes of a WBAN that is worn by the person will vary resulting in variations in the quality of wireless channels between the nodes. This can be caused by a first node (such as a hub node that is worn on a user's wrist) moving relative to a second node (such as a peripheral node that is worn on the user's waist) between a first position in which there exists a line of sight between the two nodes and so the channel quality therebetween is high, and a second position in which there is not a line of sight between the two nodes and so the channel quality therebetween is likely to be lower due to high path losses, the body's effect on antenna performance and the relative orientation and position of the antenna. For repetitive actions, such as a user walking so that their hand swings from in front of their waist to behind their waist, this can result in oscillatory variations in channel quality.

Figure 3:
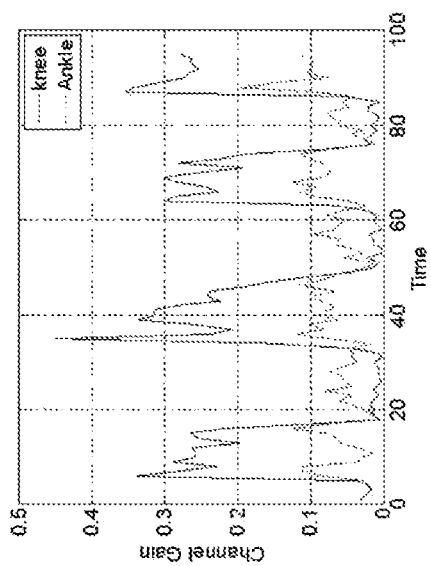
FIG. 3 shows an example of the channel gain variation with time for nodes of a WBAN.

FIG. 3 shows an example of channel gain variation with time for a wireless body area network having a hub node attached to a user's waist and peripheral nodes attached respectively to the knee and ankle of the user. As can be seen, the channel gains vary periodically as the user's knee moves relative to their hip and as their ankle moves relative to their hip during walking.

When the channel quality between two nodes is poor, it may be difficult or impossible to communicate between those nodes and so any efforts made to communicate at such times may be wasted. One way of determining when the signal quality is high enough to warrant communication between moving nodes of a WBAN would be to perform continuous real-time measuring of the channels. However, the inventors have appreciated that to do so would incur significant control signalling overheads and would result in significant energy consumption by the radio components of the nodes; accordingly, they propose herein a different approach wherein, following an initial training phase, measurements of movement are used as a proxy for channel quality and inter-node communication is performed when the motion measurement indicates that the channel quality should be favourable. When the motion measurement is such that the channel quality is not expected to be favourable, one or more nodes of the WBAN may be put to sleep by operating them in a sleep mode. An example of putting a node to sleep comprises turning off a radio component of the node and buffering data for subsequent communication when the node is awoken by turning on the radio component.

Since the energy consumption of the radio component of a WBAN node is usually higher than other components of the node, using low-power motion sensors to track body movement and using signals from the sensors to infer corresponding channel changes in order to time MAC communications enables the saving of energy (which is of particular importance for WBAN nodes which generally have limited battery supplies). Such an approach can also help to reduce communication collision, reduce control overhead and idle listening and overhearing by the nodes. In term of practical energy savings, an example of the differences in energy consumption between off-the-shelf accelerometers and a radio receiver component for embedded sensor devices can be found in Table 1. It can be seen from Table 1 that the energy consumption of the accelerometer is about 180 times less than the energy consumption of the radio component. Accordingly, by duty cycling the radio component of a WBAN node in sympathy with bodily movements, significant efficiencies can be achieved.

TABLE 1

Energy consumption comparison of accelerometer and radio receiver.

| iMEMS Accelerometers (ADXL 150 by Analog Devices Inc.) | Radio Receiver (CC2420 Texas Instruments) |
|---|---|
| 0.4 mW (75 Hz sampling frequency) | 59.1 mW |

In this disclosure, a three stage framework is proposed in order to map changes in channel characteristics to corresponding changes of one or more motion characteristics that are trackable using low complexity, low powered motion sensors such as accelerometers. In addition, since nodes in a WBAN can be placed at different parts of the body (and so may experience different motion intensities and velocities), it is not very easy to map channel changes for different nodes to the same motion pattern. Therefore, an approach for commonly indexing profiles of motion is described. The described approach provides a simple but effective mechanism to achieve synchronization of the channel periodicity of the nodes to the corresponding body motion instance (a mapping of a channel quality profile to a motion profile). In so doing, high medium access priority is given to a sensor at the time instance when good channel conditions occur. This enables a reduction in the packet drop ratio and a saving of energy on communication as transmission power or receiver sensitivity can be reduced when it is determined that such conditions occur. Furthermore, the described approach only introduces very limited overhead during its training stage, and does not require real-time assessment of channel quality during runtime operations.

There are described herein two categories of approaches for using a signal from a motion sensor to determine that the channel quality between each node of a WBAN is preferable for attempting a MAC communication between those nodes: firstly for a scenario where only a hub node is equipped with a motion sensor, and secondly for scenarios where peripheral nodes of the WBAN are equipped with motion sensors. Between the two categories of approaches, there are a number of features in common, in particular, as a first step for determining whether conditions for MAC communication between two nodes of a WBAN are variable, it is determined that a motion sensor is moving periodically. Once it has been determined that the motion sensor is moving periodically, a profile of the motion is created by recording the signal produced by the motion sensor. At this point a check may be performed to determine whether or not the recorded motion profile corresponds to a previously recorded motion profile for which an evaluation of channel quality has already been performed. In such circumstances, the recorded channel quality profile can be evaluated to determine a point at which preferable conditions exist for communication between the nodes of the WBAN. In circumstances where no comparison of the recorded motion profile is performed, or where the recorded motion profile is not found to correspond to a previously recorded motion profile, a training phase is performed.

In the training phase a profile of channel quality is created by assessing channel quality between nodes of the WBAN as the sensor moves periodically. For example, the channel quality profile may be performed by evaluating a link quality indicator, LQI, between a hub node and a peripheral node, and/or evaluating a received signal strength indicator (RSSI) between the hub node and the peripheral node and/or evaluating a signal to noise ratio (SNR) between the hub node and the peripheral node. In order that the motion profile and the channel quality profile be indexable relative to one another so that a point in the motion profile can be found based on a corresponding point in the channel quality profile, the motion profile and the channel quality profile may be acquired at corresponding points in time. Alternatively, the motion profile may be acquired at a plurality of time slots which are indexed (or labelled) by a corresponding Motion Index (MI) and the channel quality profile is then acquired at time points corresponding to the motion indices during a subsequent cycle of the periodic motion. As one example, the period of the signal produced by the motion sensor is used so as to determine a motion index within the motion profile corresponding to the current position of the motion sensor. A current motion index can be transmitted to a peripheral node from the hub node so as to enable the peripheral node to index a contemporaneously (or near contemporaneously) performed channel quality evaluation and thereby to create a channel quality profile.

The channel quality profile is then used in order to determine one or more motion indices at which conditions are suitable for wirelessly communicating between the peripheral node and the hub node. As an example, the determining step could look to identify the best channel quality in the channel quality profile and then use the motion index for that channel quality as a point for communicating between the nodes. As one possibility, instead of identifying a single time point, the approach could determine a plurality of points (MIs) for communicating between the nodes.

Examples of the approaches proposed are set out below. As the detection stage can be common to the different approaches, it is described first before the training and operation stages of the various different approaches are described separately.

Detection Stage

Figure 4:
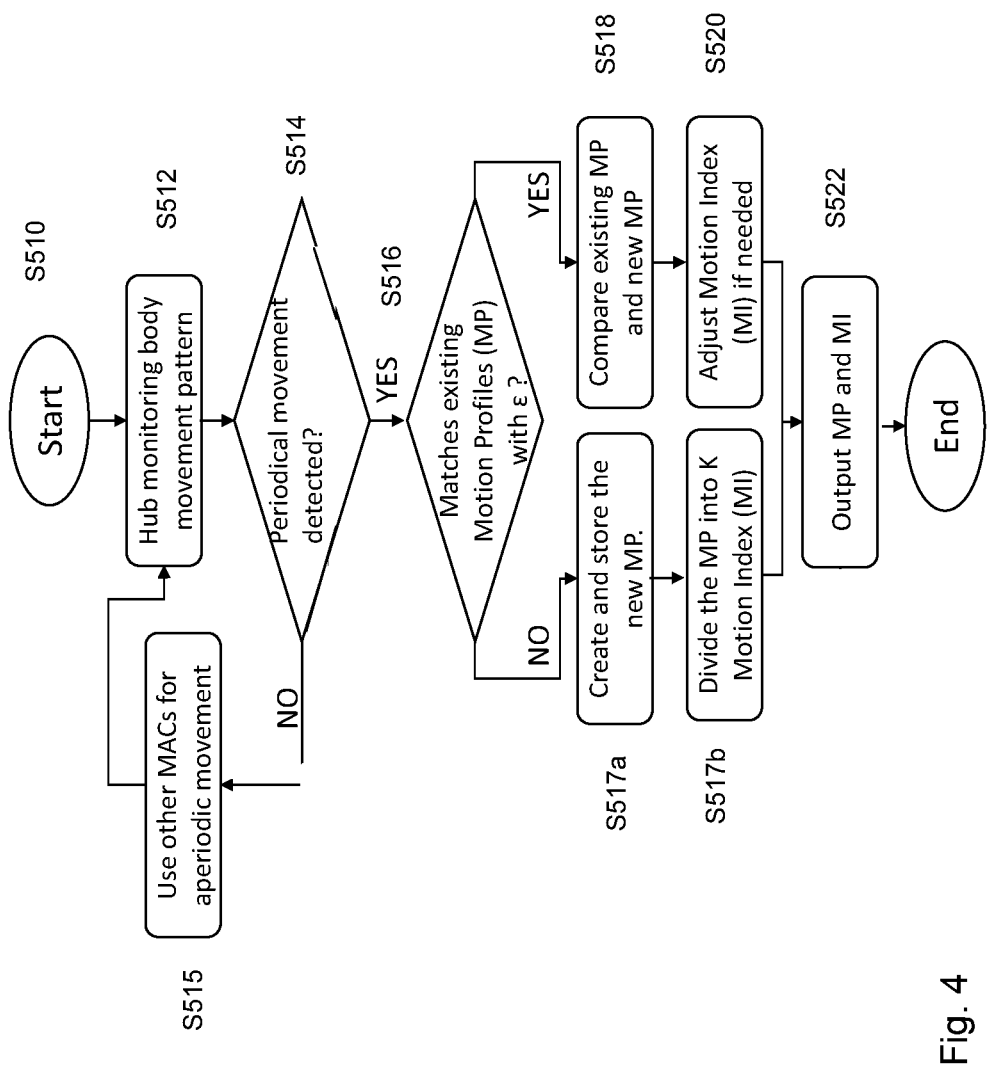
FIG. 4 shows a flow chart of example method steps for a detection phase.

FIG. 4 shows a flow chart of example method steps for the detection phase. At step S510 the method starts before proceeding to step S512 where the hub monitors the signal produced by its motion sensor. At step S514 the hub determines whether the signals provided by the motion sensor are indicative of periodic motion. This may be performed by comparing the signals produced by the motion sensor to one or more predetermined periodic motion profiles, by performing a Fourier domain analysis of the signals produced by the motion sensor, and/or by If periodical motion is not detected, then at step S515 other MACs are used for communication and the device returns to step S512 to start the process again.

If periodical motion is detected, then the method moves on to step S516 and a motion profile is created by recording the signal produced by the hub node's motion sensor at a plurality of (K) time points. An index k (where k∈K) can then be used to reference the motion profile.

Although a motion profile may be based on a single signal produced by a motion sensor, the motion profile may also be based on a plurality of signals—for example x-, y-, and z-direction accelerometer readings; additionally or alternatively, the motion profile may be based on signals provided by a plurality of sensors that are located at or in proximity to the same node.

The motion profile is then compared with a previously recorded motion profile and a similarity measure is calculated therebetween. As one example, a sum of squared differences metric is employed, although other metrics could equally be used including curve matching algorithms. Once the similarity measure has been calculated, it is compared with a predetermined threshold e and, if the value of the similarity measure with respect to ϵ indicates that the two profiles are sufficiently similar, then the method proceeds onto step S518, otherwise the method proceeds to step S517a where the new motion profile is created and stored before proceeding to step S517b where the new motion profile is divided into K motion indices. The parameter ϵ determines the tolerance level of the system for small motion changes. For example, during periodical movement of a person, small motion changes (e.g. delay or speedup in the scale of a few hundreds of ms) could be tolerable as the same motion pattern.

At step S518, the existing (previously recorded) motion profile is compared to the created one and, if the period of those two motion profiles do not coincide to within a predetermined threshold, then, at step S520, the motion index of the recorded motion profile is adjusted so as to force the recorded motion profile to be indexable by the same motion indices used by the indexed motion profile.

Only Hub Equipped with Motion Sensors

In this example, the hub node is equipped with a motion measuring sensor or sensors but the peripheral node or nodes do not necessarily have sensors. Example of such motion measuring sensors include accelerometers, gyroscopes, tilt switches, and PIR (Passive Infra-Red) sensors. Furthermore, the hub is arranged to operate in a beacon enabled mode.

Training Stage

Figure 5:
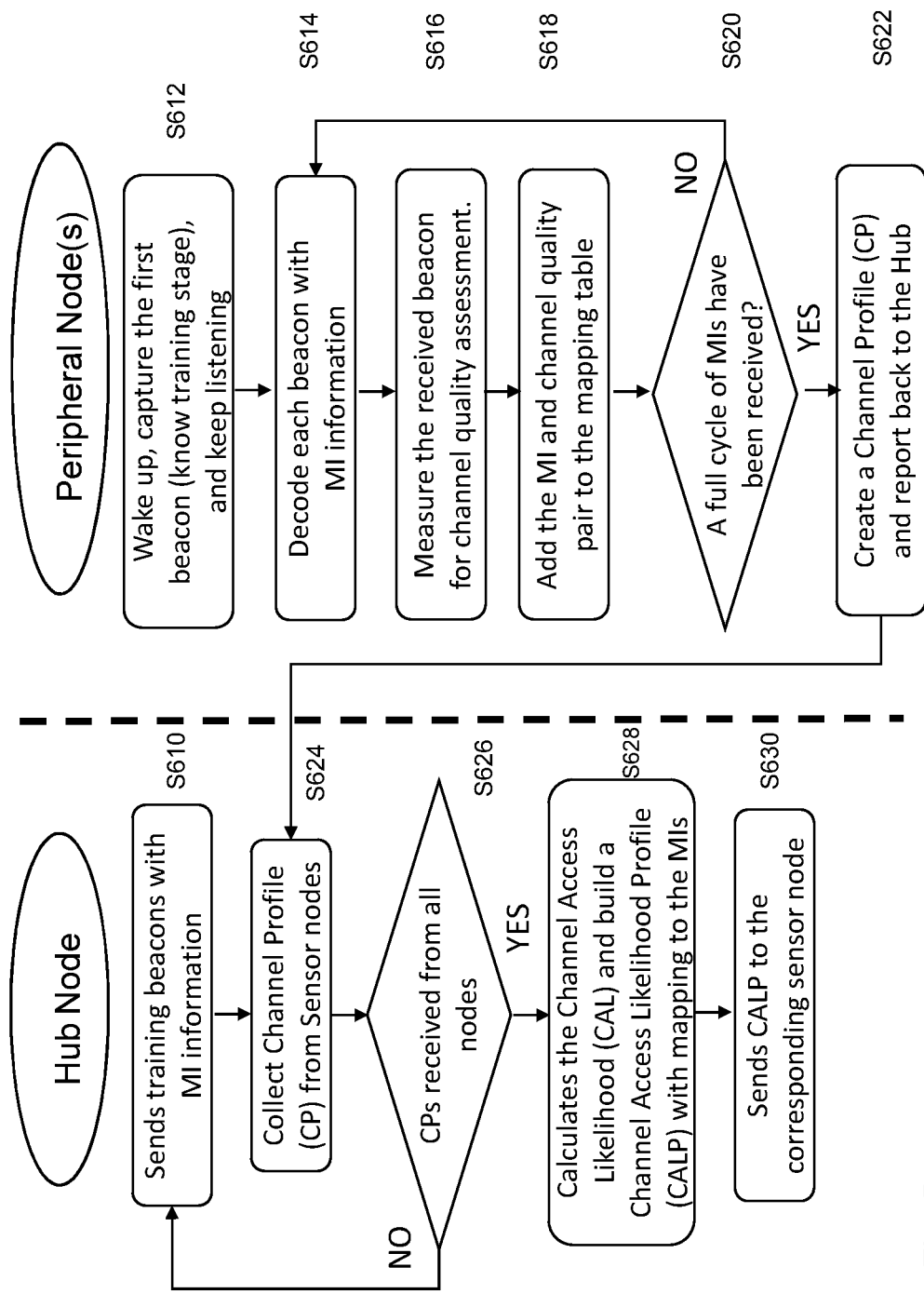
FIG. 5 shows a flow chart of example method steps performed during a training phase.

FIG. 5 shows a flow chart of example method steps performed at the hub node and the peripheral node or nodes during the training stage. At step S610, the hub node transmits beacon signals each including motion index information relating to the current position of the motion sensor at the hub node. At step S612, the (or each) peripheral node wakes up and captures the beacon (which contains motion index information) and continues to listen for subsequent beacons. The beacon may contain information (such as a training byte) to indicate that the beacon is a training beacon and may also contain information indicating the total number of motion indices contained in a full motion cycle. At step S614, the peripheral node decodes each beacon and its associated motion index information and at step S616 the peripheral node measures each received beacon in order to determine the quality of the channel between the hub node and the peripheral node. At step S618 the decoded motion index and the associated channel quality measurement are added to a table, and at step S620, the peripheral node checks whether a full cycle of motion indexes have been received and, in the event that they have not, then the method returns to step S614. At step S622 the peripheral node creates a channel quality profile and reports that back to the hub node. At step S624, the hub node collects the received channel quality profile and, at step S626, the hub node checks whether the channel quality profiles have been received from all of the peripheral nodes. If not then the method returns to step S610 and if so then the method proceeds onto step S628 where the hub node uses the channel quality profile or channel quality profiles in order to determine one or more points in the motion profile that will equate to preferable conditions for wirelessly communicating between the nodes. In this particular case, the hub node uses the received channel quality profiles to calculate a Channel Access Likelihood Profile (CALP) for each node. The CALP for each node contains a mapping table of Channel Access Likelihood (CAL) for each MI k in the motion profile of the hub node. The value of CAL can be calculated based on a few parameters, for example, channel quality, overlapping of good channels among sensor nodes, sensor data rate, criticality of the sensory data, etc. The exemplary formula below uses three of them.

$$CAL_k = \frac{C_d \times h_k}{O_k} \qquad (1)$$

Where $C_d$ is the normalized criticalness of the data, the value of which ranges between 0-1, and $h_k$ is the normalized good channel factor $$h_k = \frac{LQI_k}{\text{The best } LQI} \qquad (2)$$

Finally, $O_k$ is the overlapping factor of good channels among N sensors $$O_k = \Sigma_{i=1}^{N} G_i^k \quad (3)$$

$G_i^k=1$ if the average LQI is above a predetermined threshold that is indicative of a 'good channel' of different peripheral nodes based on their location during each MI k For a motion index k, the channel between the hub and a peripheral node i is said to be 'good', if the average LQI is above a predefined threshold, and the value of $G_i^k$ is set to 1, otherwise $G_i^k=0$. Such a MAC protocol design allows nodes to communicate with a high probability of success when the channel is less competitive.

Run-time parameters can be further used to subsequently refine the CAL values. For example, the queue size of data waiting to be transmitted in a buffer of a peripheral ($Q_{buf}$), which can be normalized and added to (1).

$$Q = \frac{Qbuf}{Buf} \quad (4)$$

Where Buf stands for the total data buffer size of the sensor.

If, for a given MI, a large number of nodes are determined to have a good channel status, then there is an increased chance of communication collision occurring in the timeslot (k) associated with that MI. To address this, a large value of $O_k$ may be used to reduce the contention probability in (1). Conversely, if only a few nodes are determined to have a good channel status for a given MI, then a smaller value of $O_k$ is produced, hence a larger value of CAL.

At step S630, the hub node sends each calculated CALP to the respective peripheral node.

The Operation Phase

Figure 6:
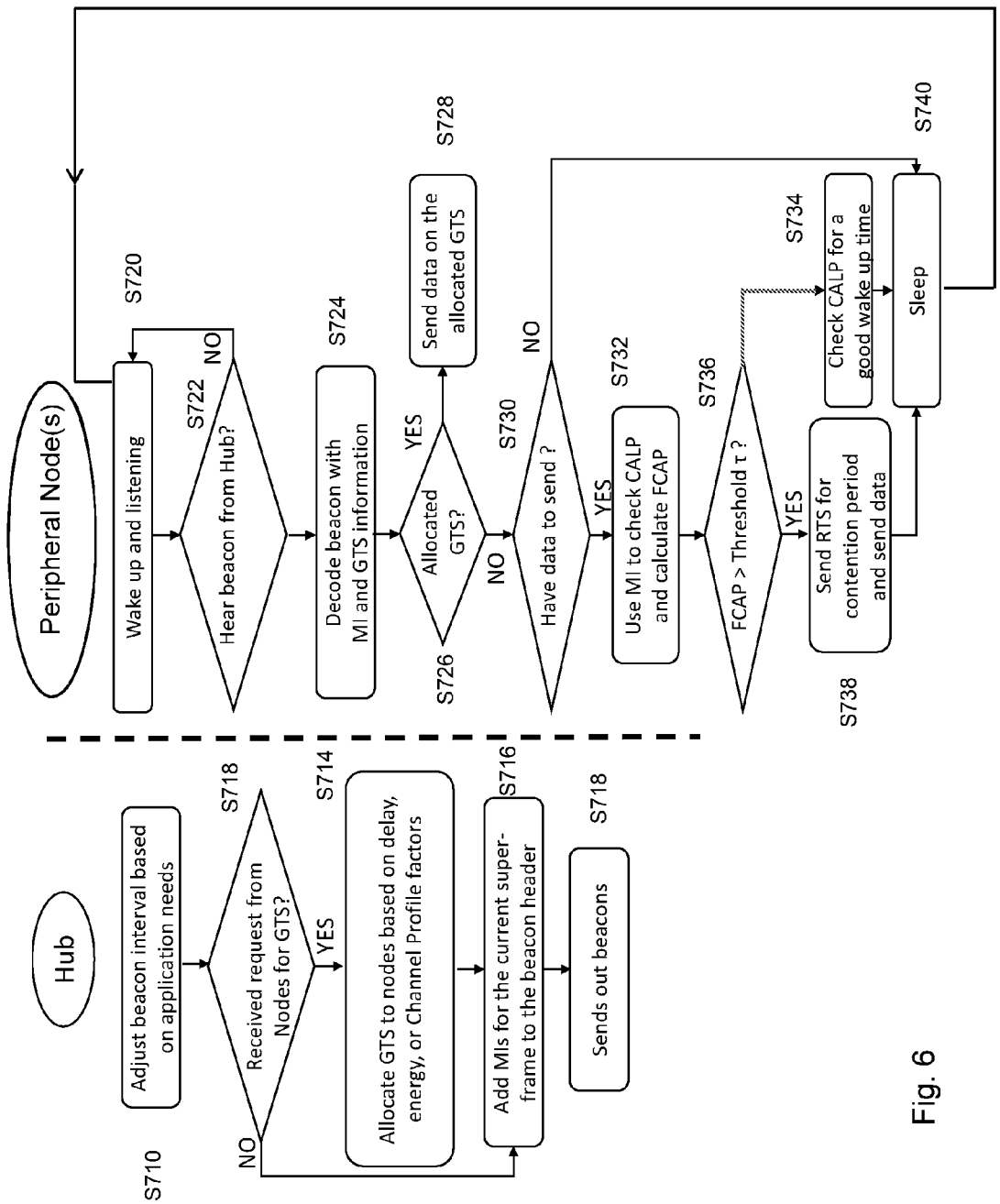
FIG. 6 shows an example flowchart of the method steps performed during an operation phase.

FIG. 6 shows an example flowchart of the method steps performed by the hub node and the peripheral node or nodes during the operation phase. At step S710, the hub node adjusts its beacon interval (the time gap that will elapse between it transmitting beacon signals) based on the needs of the application (e.g. higher data rate requires a shorter beacon interval), and also the super frame length is set to a multiple of K MI time slots At step S712, the hub node checks whether or not it has received a request for any Guaranteed Time Slots (GTS) to use for communication between the requesting peripheral node and the hub node during a contention free communication period (scheduled TDMA based access). The contention free period (CFP) with GTS and Contention Access Period are defined in the superframe structure of the IEEE 802.15.4 and IEEE 802.15.6 standard.

If GTSs have not been requested, then the method proceeds to step S716. Otherwise, at step S714, GTSs are allocated to the peripheral node (or nodes) based on the respective node's channel quality profile. As one example, for a given MI, more GTSs could be given to peripheral nodes that for which the channel quality profile is good at that MI. This can help achieve high communication reliability and energy-efficiency As transmitting packets in good channel conditions reduces the probability of packet drops thereby increasing communication reliability and reducing delay and energy consumption as the lower packet loss results in fewer MAC retransmissions.

At step S716, the next beacon that is to be transmitted by the hub node is prepared and has added to its header an MI indicative of the current position of the hub node along the motion profile. The hub node then transmits the beacon signal at step S718.

At step S720, a peripheral node wakes up and listens for a beacon signal. At step S722, if the peripheral node has received a beacon from the hub node, then it proceeds to step S724; if the peripheral node has not received a beacon from the hub node then the method returns to step S720. At step S724, the peripheral node decodes the beacon in order to extract therefrom any MI and GTS information. At step S726, the peripheral node determines whether any GTS have been allocated to it and, if so, then proceeds to step S728 and sends data at the allocated GTS. Otherwise, at step S730, the peripheral node checks whether it has any data to be sent to the hub node. If the peripheral does not have any data to be sent to the hub node then the method proceeds to step S740 and the peripheral node goes to sleep. Otherwise, at step S732, the peripheral node uses the MI to check the CALP and to calculate a Final Channel Access Priority (FCAP) which can be calculated as:

$$FCAP_k = \frac{C_d \times h_k \times Q_k}{O_k} \quad (5)$$

At step S736, the peripheral node checks whether the FCAP is above a threshold T. If so then, at step S738, the peripheral node sends a Request-To-Send (RTS) message to the hub node for the contention period (CSMA/CA contention based connection) before proceeding to step S740 and going back to sleep. Otherwise, it will go check the CALP in order to determine an appropriate time to wake up and then as step S740 go back to sleep before waking up again at step S720 at a point for which a favourable CALP is expected. Such an approach enables a reduction in synchronization overheads.

Figure 7:
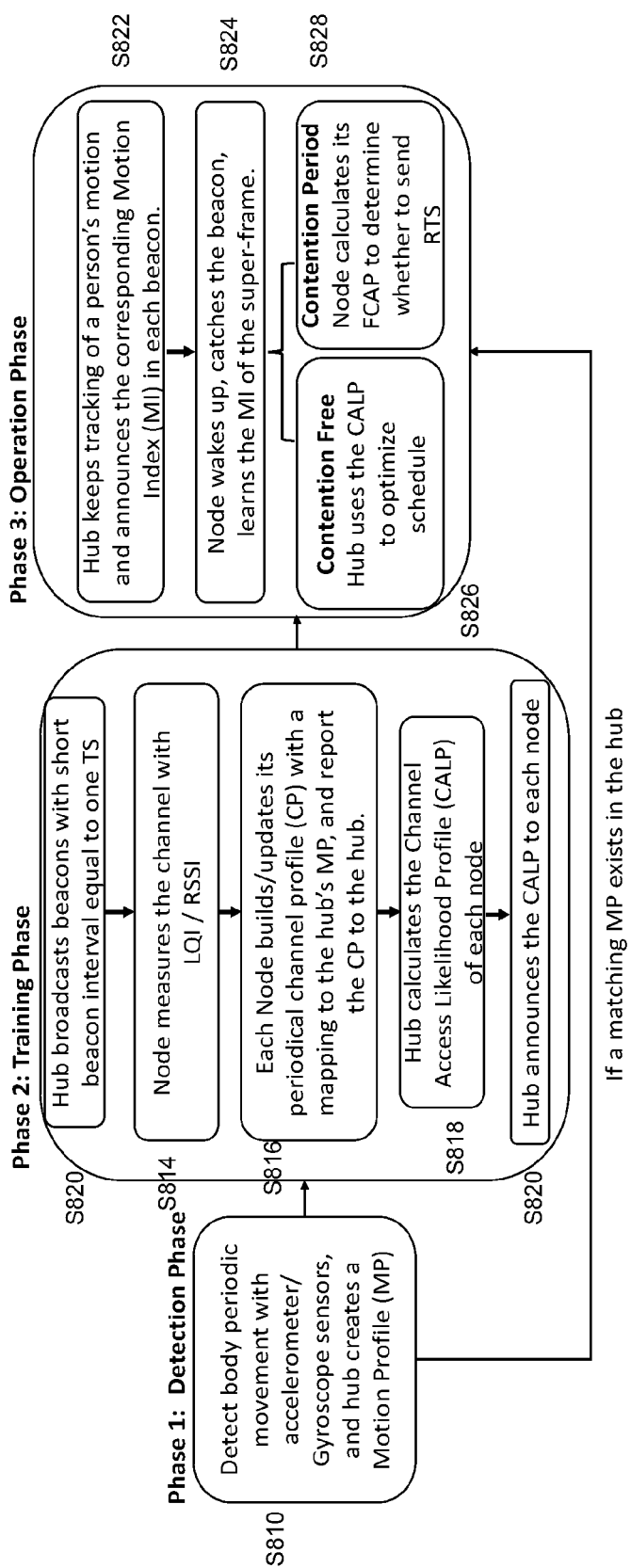
FIG. 7 shows an example flow chart of the detection, training, and operation phases for situations where only the hub node is equipped with motion sensing capability.

FIG. 7 shows an example flow chart of the detection, training, and operation phases for situations where only the hub node is equipped with motion sensing capability. At step S810, the hub node detects periodic body movement using an accelerometer and/or gyroscopic sensor and then creates a motion profile, if the motion profile is found to correspond to an existing motion profile then the method proceeds to the operation phase. Otherwise, the method proceeds to the training phase and at step S812, the hub node broadcasts a series of short beacons with the interval between them being equal to one of the time slots for which the motion profile is divided into and which can be indexed using the motion index. At step S814, a peripheral node measures the channel quality using LQI and/or RSSI measurements for the received beacons. At step S816, the peripheral node then builds up a channel quality profile that covers each motion index and reports the channel quality profile to the hub node, if the peripheral node already has a channel quality profile then that profile is updated at step S816. At step S818, the hub node calculates a CALP for each node for which it has received a channel quality profile and at step S820, the hub node sends the CALP to the respective peripheral node. At step S822 the hub node keeps track of the user's motion by monitoring the signal produced by its motion sensor and announces in each beacon a motion index indicating the point in the user's motion cycle that the user is currently at. At step S824, the peripheral node wakes up and receives the beacon transmitted from the hub node and derives from the superframe thereof the motion index along with information about the contention and contention free periods. In the event that it is determined that communications should be in a contention free period, the hub nodes uses the CALP to optimise the transmission schedule amongst the peripheral nodes and conveys the beacon indicating guaranteed time slots accordingly to the respective peripheral nodes at step S826. Alternatively, for contention periods, the peripheral node calculates an FCAP to determine whether or not to compete for communication with the hub node by sending a request to send a message to the hub node at step S828.

Hub and Peripheral Nodes Equipped with Motion Sensors—Beacon Enabled

For this approach, not only is the hub node equipped with motion measurement sensors, but also each peripheral node is equipped with such sensors, thus each peripheral node can build its own MP. Two alternatives are considered: a first in which beacons are enabled during an operation phase, and a second in which they are not. However, during the training stage, the hub node will need to broadcast beacons, and this applies to both beacon-enabled and non-beacon modes.

The detection and training phases for this approach are almost the same as for those described above in relation to the situation where only the hub node is equipped with motion sensors. The main difference being that, during the training phase, each peripheral node also creates its own Motion Profile based upon its own motion sensor readings and indexes its motion profile using an MI received in a beacon from the hub node. Motion profiles created by the peripheral node(s) are synchronised with that of the hub node as they are recorded for, and indexable by, the same MI as used by the hub node for recording and indexing its motion profile. Each peripheral node then creates its own channel quality profile and sends it to the hub node which uses the received channel quality profiles to calculate a CAL and CALP for each peripheral node before conveying these to the respective peripheral nodes.

During the operation phase, for beacon-enable mode, both the hub node and the peripheral node (or nodes) track the user's body movement by using their own motion sensors and find the corresponding motion index MI (for the hub node) and MI' (for each peripheral node). Each peripheral node further decodes the MI of the hub from the beacon. If MI and MI' do not match, it means the motion profiles of the hub node and peripheral node are not synchronized. Hence, a re-training is required. Otherwise, for non-contention periods, the peripheral node uses the beacon's GTS for scheduled data transmission and, for contention periods, computes the FCAP value in order to determine whether or not to attempt to communicate.

Figure 8:
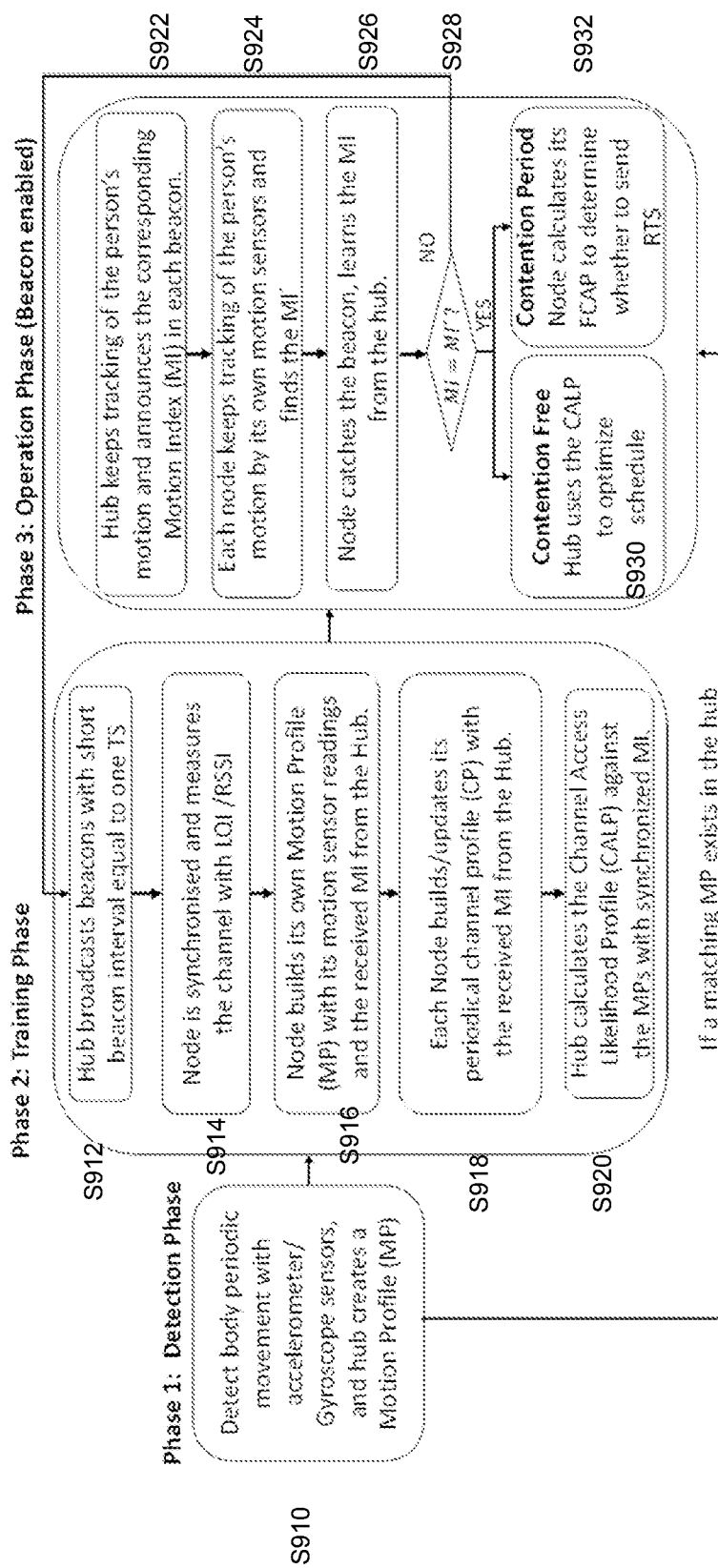
FIG. 8 shows an example flow chart of the detection, training, and operation phases for situations where the hub and peripheral nodes are equipped with motion sensors and the operation phase is beacon enabled.

FIG. 8 shows an example flow chart of the detection, training, and operation phases for situations where the hub and peripheral nodes are equipped with motion sensors and the operation phase is beacon enabled. At step S910, the hub node detects periodic body movement using an accelerometer and/or a gyroscopic sensor and then creates a motion profile. If the motion profile is found to correspond to an existing motion profile then the method proceeds to the operation phase. Otherwise, the method proceeds to the training phase and, at step S912, the hub node broadcasts a series of short beacons with the interval between the beacons being equal to one of the time slots for which the motion profile is divided into and which can be indexed using the motion index. At step S914, a peripheral node measures the channel quality using LQI and/or RSI measurements for each received beacon. The peripheral node also extracts the MI from the transmitted beacon so as to enable it synchronise itself with the hub node. At step S916, the peripheral node builds a motion profile based on signals produced by its own motion sensor readings and indexes its own motion profile using the received motion index from the hub node. At step S918, the peripheral node builds and/or updates its channel quality profile for each received MI. At step S920, the hub node receives the channel quality profiles from the peripheral nodes and calculates CALPs for each peripheral node. The Since the MI is broadcast by the hub, therefore, the method then proceeds to an operation phase and, at step S922, the hub node continues to track the motion of the user and announces a current motion index indicative of the current position of the user by sending that motion index in a beacon to the peripheral node(s). At step S924, each peripheral node keeps track of the user's motion by using its own motion sensor and so finds a motion index indicative of the current position of the motion sensor of the peripheral node (MI'). At step S926, the peripheral node receives a beacon from the hub node and extracts therefrom the hub node's current MI. At step S928, a comparison is made between MI and MI' and, in the event that MI' is not equal to MI, then the method returns to the training phase at step S912 as the hub node and peripheral node are not sufficiently synchronised. In the event that MI equals MI' then, for contention free periods, at step S930, the hub uses the CALP to schedule optimised timeslots for each of the peripheral nodes to communicate with the hub node before sending information relation to the determined GTSs to the peripheral node in a beacon. For contention periods, at step S932, each peripheral node calculates its FCAP and, based upon that calculation, determines whether or not to send a Request To Send message to the hub node.

Hub and Peripheral Nodes Equipped with Motion Sensors—Non-Beacon Enabled

This approach is similar to the approach described above for when the hub and peripheral nodes are equipped with motion sensors and the operation phase is beacon enabled. However, in contradistinction thereto, during the operation phase, periodic beacons are not transmitted by the hub node. Instead, each peripheral node of the WBAN uses a real-time measurement from its own motion sensor to find a corresponding MI before checking the CALP for that MI and computing the final FCAP. The radio component of the peripheral node is only turned on (woken up) to send a transmission request once a high FCAP value (i.e. one which exceeds a predetermined threshold) has been determined.

Figure 9:
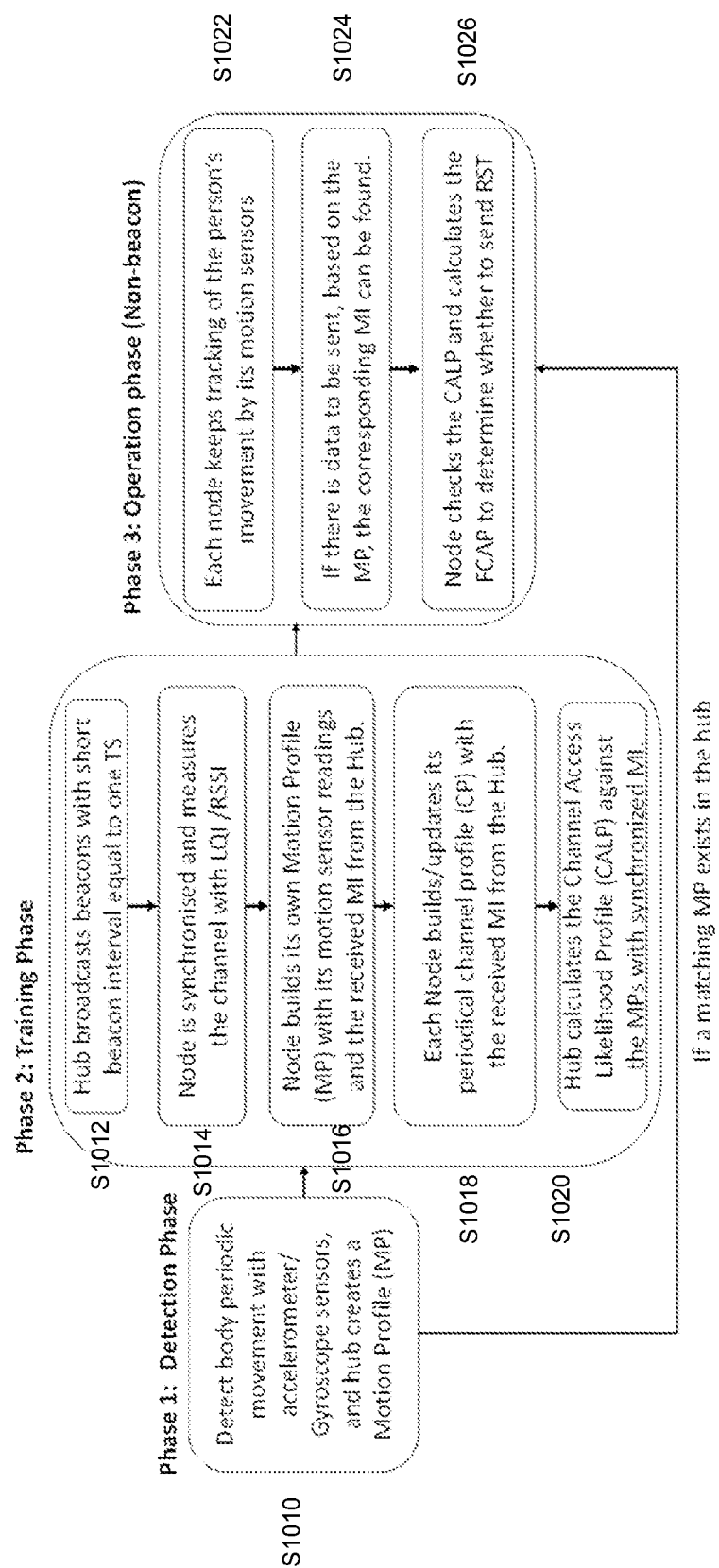
FIG. 9 shows an example flow chart of the detection, training, and operation phases for situations where the hub and peripheral nodes are equipped with motion sensors but the operation phase is non beacon enabled.

FIG. 9 shows an example flow chart of the detection, training, and operation phases for the situation where the hub and peripheral nodes are equipped with motion sensors but the operation phase is non beacon enabled. Steps S1010, S1012, S1014, S1016, S1018, and S1020 correspond respectively to steps S910, S912, S914, S916, S918, and S920 of FIG. 8 and so, in the interest of brevity, the explanation of those steps will not be repeated here. At step S1022, the peripheral node keeps track of the user's movement by monitoring the signal or signals produced by its motion sensor(s). At step S1024, if it is determined that there is data to be sent by the peripheral node to the hub node, then the signal from the peripheral node's motion sensor is used to determine at which point in the peripheral node's motion profile the node is currently at, and a corresponding MI is found. At step S1026, the peripheral node uses the determined MI to check its CALP and calculate an FCAP in order to determine whether or not to send a Request To Send message to the hub. Dependent on whether or not the Request To Send message is accepted, the peripheral node will then either attempt to communicate with the hub node or will wait before attempting to do so subsequently.

Figure 10:
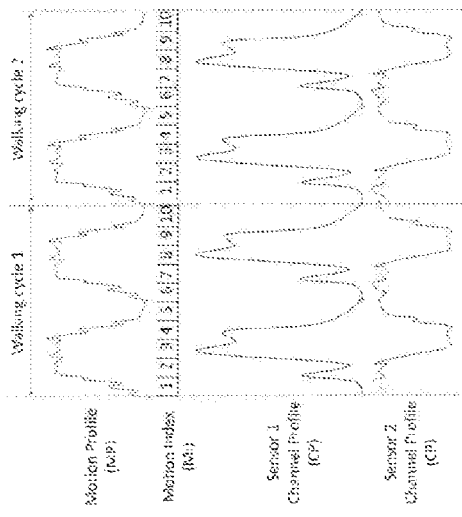
FIG. 10 shows a mapping of motion profile, motion index and channel quality profile for a case where only the hub node has a motion sensor and the hub node is arranged to communicate with two peripheral nodes.

FIG. 10 shows a mapping of Motion Profile (MP), Motion Index (MI) and Channel quality profile (CP) for a case where only the hub node has a motion sensor and the hub node is arranged to communicate with two peripheral nodes (labelled as sensor nodes 1 and 2 in FIG. 10).

Figure 11:
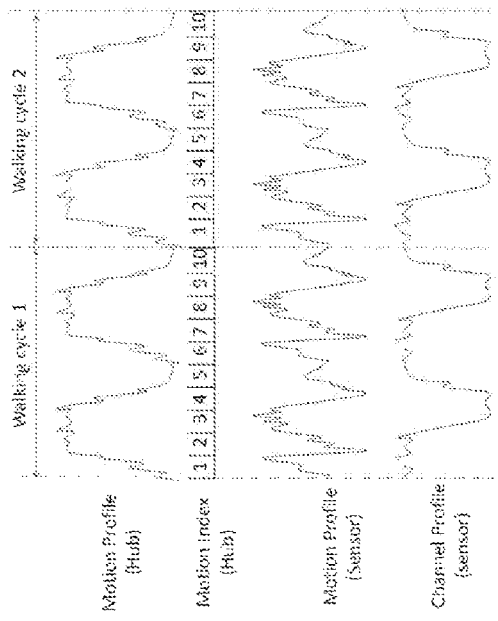
FIG. 11 shows a mapping of motion profile, motion index and channel quality profile for a case where both a hub node and a peripheral node have motion sensors.

FIG. 11 shows mapping of Motion Profile (MP), Motion Index (MI) and Channel Quality Profile (CP) for a case where both a hub node and a peripheral node have motion sensors.

As an example, Table 2 show shows an example motion profile table showing the motion measurement recordings in the same row as the corresponding motion index (MI) of that profile. A corresponding channel quality profile is shown in table 3 which shows the channel quality readings in the same row as the corresponding MI.

TABLE 2

Example of MP table

| Motion measurement readings (e.g. Accelerometer, Unit: g) | Motion Index (MI) |
|---|---|
| 0.5 | 1 |
| 0.2 | 2 |
| 0 | 3 |
| −0.2 | 4 |
| −0.5 | 5 |
| . | . |
| . | . |
| . | . |

TABLE 3

Example of CP table

| Channel quality readings (e.g. LQI, Unit: dBm) | Motion Index (MI) |
|---|---|
| −45 | 1 |
| −43 | 2 |
| −40 | 3 |
| −43 | 4 |
| −45 | 5 |
| . | . |
| . | . |
| . | . |

A person skilled in the art will appreciate that, whilst the above has described the determination that the motion sensor is moving periodically being performed at the hub node, for situations where the peripheral node is also equipped with a motion sensor, the determination of periodic motion could be performed at the peripheral node. Consequently, the creation of the motion profile could also be performed at the peripheral node. Additionally or alternatively, although the above describes the determination based on the channel quality profile of a point in the motion profile for wirelessly communicating between the nodes performed at the hub node—for example by determining a CALP thereat—the determining a point need not involve determining a CALP and could instead look to identify a maximum or minimum in the channel quality profile. Furthermore, the determining a point in the motion profile could be determined at the peripheral node instead of at the hub node.

Although the above describes the various methods steps as being performed at either a hub node or a peripheral (non-hub) node, it is disclosed herein that any of the steps could be performed at either the hub node or the peripheral node and any permutation of such steps being performed at the hub and peripheral nodes is disclosed.

As one possibility, the motion profile may be arranged so that the starting point of the motion profile (which is motion index 1) would be the lowest or highest motion sensor readings. For example, in FIG. 10, the MI 1 starts from the lowest point of the motion profile. As such points are usually turning points for changes in bodily periodical movement, close monitoring of those points can enable a determination that the period of the movement has increased or decreased; this can be done respectively by looking for an earlier than expected or later than expected maximum/minimum motion sensor reading. If those motion points are closely monitored, an adjustment of the MI can be performed if a delay or speedup performance of the movement is identified.

As the human body is a lossy medium, it can be advantageous to locate the hub node so as to reduce the amount of shadowing caused by the user's body. Indeed, locating the hub node on the user's waist or chest could prevent communication with peripheral nodes located at other parts of the user's body. As one possibility, the hub node may be configured for location on the user's wrist and reception of data from peripheral sensors mounted on other parts of the user's body—for example on the chest, waist, and/or knees. Also, as many users are used to wearing wrist watches, the introduction of a wrist mounted hub node is unlikely to inconvenience them and the location of such a hub node may facilitate maintenance—such as battery replacement or charging. Furthermore, as the wrist is a bodily extremity, and so is generally subjected to a greater range of movement than say the user's waist, a hub node located on a user's wrist may generally be subjected to a greater range of movements than one located on the user's waist. This can make it easier for motion sensors located at the hub node to detect and measure motion and may enable motion sensors of reduced sensitivity/complexity to be employed.

There is described herein a method for use within a WBAN, the method comprising creating a motion profile and a corresponding channel quality profile and using the motion profile to determining preferable conditions for MAC communication within the WBAN.

As one possibility, the approaches described herein could be employed in a distributed sensor system that is not worn by a human—for example on an articulated mechanical body.

Examples of the described approaches are set out in the below list of numbered clauses:

1. A method to configure the MAC layer protocol based on the mapping of the Motion Profile (MP) for body movement to the Channel quality profiles (CP) based on the periodicity of the channels between sensor nodes of the WBAN and the hub.
2. A method according to clause 1, wherein the Motion Profile (MP) is created by motion sensor measurements against time, and it is time slotted into motion indexes (MI).
3. A method according to clause 1, wherein the MI is broadcasted in the hub beacon. Upon received and decoded the beacon, sensor nodes of the WBAN located at the different parts of the body can learn the current motion instance via the MI, thus get synchronized to the same body motion instance.
4. A method according to clause 1, wherein the procedures and frameworks are proposed with motion sensors that are only available on the hub. It can only work in beacon-enable mode.

5. A method according to clause 1, wherein the procedures and frameworks are proposed with motion sensors that are available at both the hub and sensors on the WBAN. This solution can work either for beacon-enable mode or None-Beacon mode.
6. A method according to clause 4, wherein the Channel quality profile (CP) of each node is created in the training phase by measuring the received beacon signal and map it to the corresponding MI.
7. A method according to clause 4, wherein the hub collects all the CPs from the nodes during the training stage and calculate the Channel Access Likelihood (CAL) probability for each node, which a higher value indicates a better opportunity to access to the channel. Each CAL value is also mapped to each MI value and creates a Channel Access Likelihood Profile (CALP). The CALPs are then sent back to each node.
8. A method according to clause 7, an optimization method is proposed to calculate the CA by considering multiple parameters such as channel quality, 'good channel' overlap ratio, etc.
9. A method according to clause 4, wherein the hub adjust its beacon interval based on application during the operation phase, and announces the corresponding MI in each beacon.
10. A method according to clause 4, wherein each sensor node receives and decodes beacon during the operation phase to get the current MI and use it to further calculate Final Channel Access Probability (FCAP) based on real-time on-node information. The FCAP value determines whether a sensor node would compete to transmit in the contention period.
11. A method according to clause 5, wherein each node can create a Motion Profile (MP) by using its on-board motion sensors and the MI broadcasted by the Hub.
12. A method according to clause 5, wherein the Channel quality profile (CP) of each sensor node is measured during the training phase and is mapped to its own MP. The CPs are sent to the Hub who computes the CALP value against the MPs with synchronized MI.
13. A method according to clause 5, wherein a frame work for beacon enable mode is proposed.
14. A method according to clause 13, wherein a method of detecting possible unsynchronized MP events is proposed by matching the sensor node's MI and the decoded hub's MI from the beacon.
15. A method according to clause 5, wherein a frame work for non-beacon mode is proposed.
16. A method according to clause 15, wherein each node tracks the MI based on its own motion sensors. It then checks the corresponding CALP value and calculates the FCAP value to determine whether to wake up the radio and to perform transmission.

The approaches described herein may be embodied in any appropriate form including hardware, firmware, and/or software, for example on a computer readable medium, which may be a non-transitory computer readable medium. The computer readable medium carrying computer readable instructions arranged for execution upon a processor so as to make the processor carry out any or all of the methods described herein.

The term computer readable medium as used herein refers to any medium that stores data and/or instructions for causing a processor to operate in a specific manner. Such a storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, any other magnetic data storage medium, a CD-ROM, any other optical data storage medium, any physical medium with one or more patterns of holes or protrusions, a RAM, a PROM, an EPROM, a FLASH-EPROM, NVRAM, and any other memory chip or cartridge.

The invention claimed is:

1. A method of determining preferable conditions for Medium Access Control, MAC, communication within a Wireless Body Area Network, WBAN, having a hub node and a peripheral node, the method comprising:
   determining that a motion sensor is moving periodically;
   creating a motion profile by recording a signal produced by the motion sensor as it moves periodically;
   creating a channel quality profile based on an assessment of channel quality between the nodes of the WBAN as the motion sensor moves periodically; and
   determining, based on the channel quality profile, a point in the motion profile for wirelessly communicating between the nodes.

2. The method of claim 1, wherein the creating a channel quality profile comprises the hub node transmitting one or more beacon signals to the peripheral node and the peripheral node receiving and assessing the one or more beacon signals and optionally transmitting the results of that assessment to the hub node.

3. The method of claim 2 wherein the assessing the one or more beacons comprises assessing one or more of the following metrics for the received one or more beacons: Link Quality Indicator, LQI, Received Signal Strength Indicator, RSSI, and Signal to Noise Ratio, SNR.

4. The method of claim 1, wherein the creating a motion profile comprises recording the signal produced by the motion sensor for a plurality of time points and the creating a channel quality profile comprises assessing the channel quality for a corresponding plurality of time points so as to enable the channel quality profile to be indexed to the motion profile.

5. The method of claim 4, wherein the determining a point in the motion profile for wirelessly communicating between the nodes comprises creating, based on the channel quality profile, a Channel Access Likelihood Profile, CALP, indicative, for each of the plurality of time points, of the likelihood of successful communication between the hub node and the peripheral nodes, optionally wherein the CALP is created at the hub node and the method further comprises the hub node sending the CALP to the peripheral nodes.

6. A method of determining preferable conditions for Medium Access Control, MAC, communication within a Wireless Body Area Network, WBAN, having a hub node and a peripheral node, the method comprising:
   determining that a motion sensor is moving periodically;
   creating a motion profile by recording a signal produced by the motion sensor as it moves periodically;
   determining that the created motion profile is similar to or the same as a previously recorded motion profile in which a point for wirelessly communicating between the nodes has previously been determined based on a channel quality profile.

7. The method of claim 6, wherein determining that the created motion profile is similar to or the same as a previously recorded motion profile comprises performing an evaluation of the similarity of the created motion profile and the previously recorded motion profile and comparing the evaluated similarity to a predetermined threshold.

8. The method of claim 1, further comprising using the signal from the motion sensor to determine that the motion sensor is not at the determined point and consequently putting a radio component of the peripheral node into a sleep mode.

9. The method of claim 1, further comprising using the signal from the motion sensor to determine that the motion sensor has moved to the determined point and consequently attempting to wirelessly communicate between the nodes, optionally further comprising waking up a radio component of the peripheral node so as to exit a sleep mode consequent to determining that the motion sensor has moved to the determined point and prior to the attempting to wirelessly communicate between the nodes.

10. The method of claim 9, wherein the using the signal from the motion sensor to determine that the motion sensor has moved to the determined point comprises:
    the hub node transmitting a beacon signal containing indexing information indicative of a point within the motion profile that corresponds to the signal currently produced by the motion sensor; and
    the peripheral node:
        receiving the beacon signal containing indexing information,
        using the indexing information to identify a point within the channel quality profile or a profile derived therefrom, and
        determining that the identified point corresponds to the determined point.

11. The method of claim 9, wherein the motion sensor is at the hub node and so the motion profile is a hub node motion profile, the method further comprising creating a peripheral node motion profile by recording a signal produced by a motion sensor at the peripheral node as it moves periodically, wherein the using the signal from the motion sensor to determine that the motion sensor has moved to the determined point comprises:
    the hub node transmitting a beacon signal containing indexing information indicative of a point within the hub node motion profile that corresponds to the signal currently produced by the hub node motion sensor;
    indexing the peripheral node motion profile using the indexing information and determining that the indexed point within the peripheral node motion profile corresponds to the signal currently produced by the peripheral node motion sensor;
    using the indexing information to identify a point within the channel quality profile or a profile derived therefrom, and
    determining that the identified point corresponds to the determined point.

12. The method of claim 4, wherein the motion sensor is at the hub node and so the motion profile is a hub node motion profile, the method further comprising creating a peripheral node motion profile by recording, for a plurality of time points corresponding to the plurality of time points for which the channel quality profile was assessed, a signal produced by a motion sensor at the peripheral node as it moves periodically, the method further comprising using the signal from the peripheral node motion sensor to determine that that motion sensor has moved to the determined point and consequently attempting to wirelessly communicate between the nodes, optionally further comprising waking up a radio component of the peripheral node so as to exit a sleep mode consequent to determining that the peripheral node motion sensor has moved to the determined point and prior to the attempting to wirelessly communicate between the nodes.

13. An apparatus or system arranged to perform a method, the method comprising:
    determining that a motion sensor is moving periodically;
    creating a motion profile by recording a signal produced by the motion sensor as it moves periodically;
    creating a channel quality profile based on an assessment of channel quality between the nodes of the WBAN as the motion sensor moves periodically; and
    determining, based on the channel quality profile, a point in the motion profile for wirelessly communicating between the nodes.

14. A non-transitory computer readable medium comprising machine readable instructions arranged, when executed by one or more processors, to cause the one or more processors to carry out a method, the method comprising:
    determining that a motion sensor is moving periodically;
    creating a motion profile by recording a signal produced by the motion sensor as it moves periodically;
    creating a channel quality profile based on an assessment of channel quality between the nodes of the WBAN as the motion sensor moves periodically; and
    determining, based on the channel quality profile, a point in the motion profile for wirelessly communicating between the nodes.

* * * * *